(12) United States Patent
Schmid

(10) Patent No.: US 6,620,864 B2
(45) Date of Patent: Sep. 16, 2003

(54) EPOXY COMPOUNDS FOR USE IN DENTAL MEDICINE AND/OR DENTISTRY

(75) Inventor: Adalbert Schmid, Rebstein (CH)

(73) Assignee: LSP Dental Chemistry AG, Heerbrugg (CH)

(*) Notice: Subject to any disclaimer, the term of this patent is extended or adjusted under 35 U.S.C. 154(b) by 0 days.

(21) Appl. No.: 09/932,215

(22) Filed: Aug. 17, 2001

(65) Prior Publication Data

US 2002/0040103 A1 Apr. 4, 2002

Related U.S. Application Data

(63) Continuation of application No. PCT/CH00/00085, filed on Feb. 14, 2000.

(30) Foreign Application Priority Data

Feb. 17, 1999 (EP) .............................. 99810139

(51) Int. Cl.$^7$ .............................. C08K 3/10; C08L 63/02
(52) U.S. Cl. ................. 523/457; 433/226; 433/228.1; 522/31; 522/32; 522/66; 522/67; 522/170; 522/980; 523/458; 523/466
(58) Field of Search ............................ 522/31, 32, 66, 522/67, 170, 980; 433/226, 228.1; 523/457, 458, 466

(56) References Cited

FOREIGN PATENT DOCUMENTS

| EP | 0 509 516 A2 | 10/1992 |
| WO | WO 98/47046 A1 | 10/1998 |
| WO | WO 98/47047 A1 | 10/1998 |

OTHER PUBLICATIONS

Shimbo et al; Effects of Tertiary Amine Accelerators on Curing of Expoxide Resins; 24 *J. of Polymer Sci.* Sep. 24, 1986 p 1932–1941.

Davidenko et al; Development of New Photopolymerisable Dental Sealants; 129 *Clinical Abstracts,* No. 280964 Nov. 23, 1998.

Brauer et al; New Amine Accelerators for Composite Restorative Resins; 92 *Chemical Abstracts,* No. 99541 Mar. 24, 1980.

*Primary Examiner*—Robert Dawson
*Assistant Examiner*—D. Aylward
(74) *Attorney, Agent, or Firm*—Schweitzer Cornman Gross & Bondell LLP

(57) ABSTRACT

A composition suitable for use in dental medicine and/or dentistry polymerizable by cationic polymerization consists of one or more epoxy compounds, a plasticizer, a catalyst for hardening by ring opening, a catalyst for hardening by light and an accelerator consisting of a non alkaline tertiary amine. At radiation with a light having a wavelength of 340–500 nm the composition hardens practically free of contraction and adhesiveness.

10 Claims, No Drawings

EPOXY COMPOUNDS FOR USE IN DENTAL MEDICINE AND/OR DENTISTRY

This application is a continuation of PCT/CH00/00085 of Feb. 14, 2000.

The invention refers to epoxy compounds containing composition polymerizable by light for use in dental medicine and/or dentistry, consisting of one or more epoxy compounds, a plasticizer, a catalyst for hardening by ring opening, a catalyst for hardening by light and an accelerator.

BACKGROUND OF THE INVENTION

It is known to prepare compositions on basis of acrylates applicable in dental medicine which can be hardened by radical polymerization using ultraviolet and visible light. These compositions have the disadvantage of shrinking strongly at hardening, and the hardened material has abrasion and solidity problems. Further it is known to prepare epoxy compounds containing compositions, which can undergo cationic polymerization with low shrinkage. In this case it is however necessary to use for such a polymerization a light source with high energy, e.g. a e-non/mercury vapor lamp, which can not be used in medical practices because of danger of combustion. Moreover, the known hardened composition does not fulfill the requirements for freedom of adhesiveness and abrasiveness. To achieve a complete hardening it is necessary to apply a thermic after-treatment, which is not practicable in the mouth of a patient.

From Minnesota Mining disclosure WO-A-98/47047 it is known to harden a composition obtained by the combination of a cyclic diepoxide, tetrahydrofurane, diphenyliodoniumhexa-fluorantimonate and camphor quinone by means of accelerators (e.g. 4-dimethylaminobenzaldehyde, 4-dimethylaminophenethanol, di-hydroxyethyl-p-toluidine, ethyl-4-dimethylaminobenzoate) at wavelengths of 400 to 1000 nm. The so-obtained materials can be used as dental material. The broad scope of claim 1 of WO-A-98/47047 covers accelerators for hardening of the above compositions wherein the p-amino group of a p-aminobenzoic acid alkyl ester is substituted by one or two hydroxyalkyl groups. However, the last mentioned compounds are claimed as accelerators in a broad sense only, and there is no evidence that a compound of this group has ever been investigated or used for the acceleration of hardening.

BRIEF DESCRIPTION OF THE INVENTION

According to the invention it has been found that the N,N-bis-hydroxyalkyl-p-aminobenzoic acid alkyl esters have an excellent efficacy as accelerators of the light induced hardening of a composition comprising one or more epoxy compounds, a plasticizer, a catalyst for ring opening and a catalyst for hardening by light.

It is therefore a purpose of the present invention to provide epoxy compounds containing compositions for use in dental medicine and/or dentistry which are free of the disadvantages of acrylate compositions, and which are hardenable by light polymerization practically without shrinkage, have a smooth, abrasion-proof surface, and which are moreover not adhesive. The surface of the hardened composition should not discolor and should inhibit bacterium deposits. Moreover, the composition does not deliver toxic substances to a cavitation during filling or on a surface during hardening.

Further, it is a purpose of the invention to provide epoxy compounds containing compositions for use in dental medicine and/or dentistry, wherein the accelerator used for hardening displays an outstanding efficacy by hardening the composition in the shortest time possible.

These purposes are achieved by the use of a polymerizable composition containing one or more epoxy compounds, a plasticizer, a catalyst for ring opening, a catalyst for hardening by daylight using as an accelerator a p-amoniobenzoic acid alkyl ester N,N-disubstituted by hydroxyalkyl groups.

The advantage of the present invention lies in the fact that a composition containing one or more epoxy compounds can be hardened using conventional dentist lamps in the shortest time possible in such a way that a polymer is obtained which is practically free of shrinkage, has an adhesive free surface, and which does not need any further after treatment.

The composition according to the invention polymerizes with a very smooth surface, by which bacteria deposits are inhibited. Unless otherwise indicated, all percentages are on a weight percentage basis in this specification.

DETAILED DESCRIPTION OF THE INVENTION

Epoxy Compounds

In the composition according to the invention, the epoxy compounds can be selected from the group consisting of oligomers, which can be polymerized by cationic ring opening e.g. cycloaliphatic epoxides, cycloaliphatic diepoxides, oxetanes, oxetan-silanes, epoxilated vinyl ethers, bisphenol-A-epoxides, bisphenol-F-epoxides, bisphenol-A-F-epoxides, epoxy novolakes, phosphacenes, silicones, phosphonites, isoxazoles, ethers, thioethers, lactones and lactames, which are present in an amount of 20 to 95%, and preferably to 90% relative to the total amount of the composition.

Plasticizers

Besides the epoxy compounds, the composition additionally contains plasticizers, which are selected from the group consisting of polyols, alkyl glycidyl esters, 1,7-diepoxy octone, 1,4-butandioldiglycidyl ester, vinylcyclohexenediol, limonendioxide, tetrahydrofurane, polytetrahydrofurane mw. 220–2000, caprolacton, glycidol, mono-, di- and multifunctional alcohols, propylenglycol, butandiol, butoxyethanol and hydroxyfonctional compounds, which are present in an amount of 1 to 30%, preferably 10%, based on the total amount of the composition.

Catalysts

The hardening by ring opening takes place by means of cationic catalysts, which are selected out of the group comprising ferrocenium salts, cyclic sulfonium salts, onium salts, diarylhalonium salts, aryldiazonium salts, triarylsulfonium salts, diaryliodonium salts, and aromatic and/or aliphatic iodonium salts, which are present in an amount of 0,1 to 8%, preferably 2%, based on the total weight of the composition. The hardening of the composition by daylight takes place with the aid of catalysts, which are selected out of the group comprising camphor quinone phenanthren quinone, glyoxal, 5,7 diiodo-3-butoxy-6-fluorone, biacetyl, 3,3,6,6-tetramethyl-cyclohexandione, benzil, photoinitiators of the flouron series, 3,6-dihydoxyxanthone, hydroperoxide, dibenzoylperoxide and cumolperoxide, which are present in an amount of 0.01 to 3%, preferably 0.2%, based on total weight of the composition.

Accelerators

The accelerators used according to the invention are p-aminobenzoic acid esters N,N-disubstituted by hydroxyalkyl groups. They can be selected from the group comprising ethyl-N,N-di-hydroxypropyl-p-aminobenzoate and ethyl-N,N-di-hydroxyethyl-p-aminobenzoate.

Especially preferred catalysts for their advantageous properties are hydroxyalkyl groups N,N-disubstituted p-amino-benzoic acid alkyl esters, such as ethyl N,N-di hydroxypropyl-p-aminobenzate, especially 4-[bis(2-hydroxypropyl)amino]benzoic acid ethylester, and ethyl N,N-dihydroxyethyl-p-amino-benzoate, especially 4-[bis(2-hydroxyethyl)amino]benzoic acid ethylester.

Likewise very useful are accelerators of the type of hydroxyalkyl (mono) or (poly)oxyalkylen group N,N-disubstituted-p-aminobenzoic acid alkyl- or alkyl (mono) or (poly)oxyalkylenesters, especially the ω-ethylpoly(oxyethylen)-4-[bis{ω-(2-hydroxyethyl)poly(oxyethylen)-amino]-benzoate, also known under the name PEG-25-PBA.

Surprisingly it has been found that the last mentioned accelerators are useful at the same time as light stabilizers and color stabilizers. The alkyl esters and alkyl(mono) or (poly)oxyalkylene esters of the benzoic acid mentioned in this connection comprise of course also alkyl esters and alkyl(mono) or (poly)oxyalkylen esters substituted by halogen, hydroxyl groups etc. The hydroxyalkyl groups used here for the N,N-disubstitution contain one or more hydroxyl groups, whereby the alkyl group contains 1 to 6, and preferably 1 to 4, carbon atoms.

The accelerators are present in the composition according to the invention, in an amount of 0.1 to 5%, preferably of 0.4%, based on the total weight of the composition.

In accordance with the present invention, the polymerization of the present compositions occurs by means of light with a wavelength of 340–500 nm, preferably 480 nm.

Other Ingredients

The composition according to the invention may further contain filler materials which are suitable for medical use. A useful filler material is, for example, fine-grained silicon dioxide, preferably X-ray opaque glass, like barium and strontium glass, silica glass and titanium dioxide. Such fillers may comprise 5–85% by weight, based on the total weight of the composition. Titanium dioxide, in an amount of 0.1 to 10% may be used as a sealant. In composites, silica glass and/or X-ray opaque glasses, like barium and strontium glass, can be used individually or together in an amount of 20–75%, based on the total weight of the composition. By addition of the filler materials the hardness of the polymerized composition is considerably increased.

Further, the composition may contain coloring pigments, and/or color and light stabilizers.

The preparation of the composition according to the invention is effected by mixing the components in the given amounts as described. The components are individually known or can be prepared from known starting materials in a known manner.

The following examples serve to illustrate the invention more closely without restricting its content or scope.

EXAMPLES

Example 1

| Component | Amount in grams |
| --- | --- |
| Cycloaliphatic diepoxide[1] | 85.00 |
| Tetrahydrofurane | 08.50 |
| Cationic catalyst[4] | 03.00 |
| 4-[Bis(2-hydroxypropyl)-amino]-benzoic acid ethyl ester[18] as accelerator | 00.80 |
| light hardening catalyst | 00.20 |

Result

After 60 sec. exposure to a commercial Litema halogen lamp the Barcol hardness is 65. In the boiling test the hygrostability is excellent.

Example 2

| Component | Amount in grams |
| --- | --- |
| Cycloaliphatic diepoxide[1] | 85.00 |
| Epoxisilane | 11.80 |
| Cationic catalyst[4] | 02.50 |
| 4-[Bis(2-hydroxypropyl)-amino]-benzoic acid ethyl ester[18] as accelerator | 00.50 |
| light hardening catalyst (camphor quinone))[7] | 00.20 |

Result

After 60 sec. exposure to a commercial Litema halogen lamp the Barcol hardness is 50.

Example 3

| Component | Amount in grams |
| --- | --- |
| Cycloaliphatic diepoxide[1] | 85.00 |
| Epoxisilane | 11.80 |
| Cationic catalyst[4] | 02.50 |
| 4-[Bis(2-hydroxyethyl)-amino]-benzoic acid ethyl ester[18] as accelerator | 00.50 |
| light hardening catalyst (camphor quinone)[7] | 00.20 |

Result

After 60 sec. exposure to a commercial Litema halogen lamp the Barcol hardness is 65, whereby the composition is already hardened after 5 sec.

Instead of the accelerators described in Examples 1 to 3, the following accelerators can be used in the stated compositions in the given amounts with good success:

4-[(2-Hydroxypropyl)-(3-hydroxypropyl)-amino]-benzoic acid-butyl ester;

3-[(4-Hydroxybutyl)-(2-hydroxyethyl)-amino]-benzoic acid propyl ester;

2-[(2-Hydroxypropyl)-(2-hydroxyethyl)-amino]-benzoic acid methylester;

4-[Bis(4-hydroxypentyl)-amino]-benzoic acid hexyl ester;

3-[(3-Hydroxybutyl)-(3-hydroxypropyl)-amino]-benzoic acid pentyl ester;

4-[Bis(3-hydroxypropyl)-amino]-benzoic acid propyl ester;
3-[(2,4-Dihydroxybutyl)-(2,3-dihydroxypropyl)-amino]-benzoic acid methyl ester;
4-[(3-Hydroxypropyl)-(2,3-dihydroxybutyl)-amino]-benzoic acid butyl ester; and
ω-Ethylpoly(oxyethylen)-4-[bis {ω-(2-hydroxyethyl)poly(oxyethylen)}-amino]benzoate (PEG-25-BPA)
(whereby this accelerator has shown only a low activity).

Example 4

| Component | Amount in grams |
|---|---|
| Cycloaliphatic diepoxide[1] | 70.00 |
| Polyol[2] | 20.00 |
| Epoxylated silane[3] | 02.00 |
| Cationic catalyst[4] | 02.00 |
| Stabilizer[5] | 00.50 |
| Tertiary amine as accelerator[6] | 00.10 |
| Catalyst for light hardening[7] | 00.20 |
| Color stabilizer[8] | 00.10 |

Result

With a commercial hardening lamp (Trademark Translux Cl from Kulzer, Frankfurt a. M.) dry polymers are obtained within 30 sec., inhibiting bacterium deposits. The Barcol hardness is 45. In a color stability test no discolorations have been observed.

Example 5

| Component | Amount in grams |
|---|---|
| Bisphenol A epoxide[9] | 80.00 |
| Polyol[10] | 15.00 |
| Cationic catalyst[4] | 02.00 |
| Tertiary amine as accelerator[6] | 00.00 |
| Stabilizer[5] | 00.50 |
| Light stabilizer[11] | 00.40 |
| Epoxylated silane[3] | 02.00 |
| Catalyst for light hardening[7] | 00.20 |

Result

With the Translux CL hardening lamp a solid elastic polymer is obtained after 60 sec. exposure with a Barcol hardness of 25 and excellent color stability. When applying the composition to cleaned steel plates, it will be hardened within 60 sec. by means of the Denta-color hardening device and subsequently bent in an angle of 90°. No detachments or fissures can be detected on the bend and the whole plate. The sealant gives an excellent bond. Sealants hardening by means of radical polymerization lead in the same test to an instantaneous detachment of the coating.

Example 6

| Component | Amount in grams |
|---|---|
| Cycloaliphatic diepoxide[1] | 80.00 |
| Vinyl ether[12] | 15.00 |
| Epoxylated silane[3] | 02.00 |
| Cationic catalyst[4] | 03.00 |

-continued

| Component | Amount in grams |
|---|---|
| Tertiary amine as accelerator[6] | 00.10 |
| Light stabilizer[13] | 00.50 |
| Catalyst for light hardening[7] | 00.30 |

Result

The mixture hardens with the Translux CL lamp within 5 sec. with a layer thickness of 5 mm. The high reactivity of this formulation leads to a brownish discolored, brittle polymer. A very strong heat generation takes place with temperatures to 180° C.

Example 7 (composite)

| Component | Amount in grams |
|---|---|
| Composition of Example 1 | 25.00 |
| Ba-Al Borosilicate glass[14] | 45.00 |
| Siliciumdioxide[15] | 30.00 |
| Colours[16] | 00.05 |

Result

The obtained tooth filling material (composite) hardens with the Translux CL lamp within 60 sec. in a thickness of the layer of 4.5 mm. Color plates made out of it could reproduce the coloring in the chosen Vita color, and the transparency corresponds to the commercial filling raw material. The flectional strength is 120 Pa/mm². The modulus of elasticity is determined to be 14700 MPa. The Barcol hardness is 82. Of the polymer of Example 7 the contraction force and the linear contraction has been determined, resulting out as follows:

| Component | Linear (Micron) | Force (kp) | Vol (%) |
|---|---|---|---|
| Polymer of example 7 | 9.5 | 1.3 | 0.7 |
| Tetric commercial product | 29.2 | 3.7 | 2.4 |
| MHC finest hybrid composite | 31.6 | 4.4 | 3.1 |

Result

The contraction measurements prove that the materials according to the invention are contracting with a factor of 3 less than the materials of the usual prior art, e.g. they are hardening practically without contraction and display in the same scale substantial lower contraction forces.

Example 8

| Component | Amount in grams |
|---|---|
| Composition according to example 4 | 95.00 |
| Titanium dioxide[17] | 05.00 |

Result

The hardening with the Translux CL lamp yields within 30 sec. on a human eye-tooth which has been previously treated with a 35% phosphoric acid a scratch-resistant, opaque, white sealing. Compared with a sealing material on the market the polymer obtained according to the invention has a layer which inhibits the bacteria deposits.

Example 9

| Component | Amount in grams |
| --- | --- |
| Composition according to Example 4 | 80.00 |
| Radically hardening composition | 20.00 |

Result

The hardening occurs within 30 sec. by means of the Translux CL lamp. The surface contains a small inhibiting layer, on which a commercial composite is polymerised, yielding a stable composite.

Comparative Examples

Example 10

Component

Composition of Example 4 without addition of a tertiary amine accelerator.

Result

At radiation with the Translux CL lamp it was not possible to obtain an adhesive free layer even after an exposure time of 5 minutes. At exposure in a Dentacolor stove (source of high energy) an adhesive free, elastic polymer is obtained. At afterbaking in a warming cupboard at 90° C. during 60 minutes the polymer becomes solid. Barcol hardness is 45.

Example 11

Component

Resin mixture of Example 4 treated with diethylaminomethylmethacrylate (radicalic accelerator).

Result

Hardening with the Translux CL lamp is not possible. The cationic catalyst system is deactivated. Also other alkaline amines, like triethanolamine or methacrylated amines, deactivate the system.

Significance of the Exponents Used in the Above Examples

[1] Obtainable from Degussa AG in D-6450 Hanau, under the specification K 126.
[2] Triethylenglycol from Fluka AG, in CH-9471 Buchs.
[3] Glymo from ABCR GmbH in D-76151 Karlsruhe.
[4] Diphenyljodoniumhexafluorantimonate from 3M, USA; or Th. Christ AG in CH-4153 Reinach.
[5] Tinuvin from CIBA Specialty Chemicals in CH-4057 Basel.
[6] Tetramethylaniline from Aldrich USA, or Fluka AG in CH-9471 Buchs.
[7] Camphor quinone from Aldrich USA, or Fluka AG in CH-9471 Buchs.
[8] Octyl-dimethyl-p-aminobenzoate from Amercol in B-1800 Vilvoorde.
[9] Araldit from CIBA Spezialitätenchemie AG in 4002 Basel.
[10] Tetrahydrofuran from Fluka AG in CH-9471 Buchs.
[11] PEG-25-p-aminobenzoate from BASF AG in D-76056 Ludwigshafen.
[12] CHVE from ISP in Wayne N.J. 0740, USA.
[13] Amerscreen P from Amercol in B-1800 Vilvoorde.
[14] Obtainable from Esschem in Essington, Pa. 19029 USA.
[15] Obtainable from Degussa AG in D-6450 Hanau.
[16] Obtainable from BASF AG in D-76056 Ludwigshafen.
[17] DAB from Fluka AG in CH-9471 Buchs.
[18] Obtainable from Frinton Laboratories Inc. in Vineland N.J. 08362, USA.
[19] Obtainable from Frinton Laboratories Inc. in Vineland N.J. 08362, USA.

The compositions according to the invention have a potential which enables them to solve successfully many unsolved problems in odontology and in the dentist's laboratory. Combining the present invention with prior art systems, such as radical polymerizable systems, broadens potential applications, such as multiple-layer techniques, great constructions, raw materials for reparations etc.

Clinical investigations with the composition of the present invention have proven their outstanding suitability in odontology. The compositions according to the invention may be used as amalgam replacements without the disadvantages of the metal.

Various other modifications to the present invention will suggest themselves to those skilled in the art and should be deemed within the spirit of the present invention.

I claim:

1. An epoxy compound-containing composition polymerizable by light for use in dental medicine and/or dentistry, consisting of one or more epoxy compounds, a plasticizer, a catalyst for hardening by ring opening, a catalyst for hardening by light and an accelerator chosen from the group consisting of ethyl-N,N-dihydroxypropyl-p-aminobenzoate and ethyl-N,N-dihydroxyethyl-p-aminobenzoate.

2. The epoxy compound-containing composition according to claim 1, characterized in that the accelerator is used in an amounts of 0.1 to 5% related to the total weight of the composition.

3. The epoxy compound-containing composition according to claim 2, characterized in that the accelerator is used in an amount of 0.4%, related to the total weight of the composition.

4. The epoxy compound-containing composition according to claim 1, characterized in that the polymerization is effected by means of light with a wavelength of 340–500 nm.

5. The epoxy compound-containing composition according to claim 1, wherein the composition contains filler material suitable for medical use.

6. The epoxy compound-containing composition according to claim 5, wherein the filler material is selected from the group consisting of fine grained silicon dioxide, X-ray opaque glass, barium or strontium glass, silica glass and titanium dioxide.

7. The epoxy compound-containing composition according to claim 5, wherein the filler material is present in an amount of 5–58% by weight, based on the total weight of the composition.

8. The epoxy compound-containing composition according to claim 5, containing additionally a titanium dioxide sealant in an amount of 0.1 to 10% by weight, and at least one member of the group consisting of silica glass, X-ray opaque glasses, barium and strontium glass, and fine grained silicon dioxide, present in an amount of 20–75% by weight, based upon the total weight of the composition.

9. The epoxy compound-containing composition according to claim 1, further comprising at least one of coloring pigments and color and light stabilizers.

10. The epoxy compound-containing composition of claim 6, wherein the filler material is present in an amount of 5–58% by weight, based upon the total weight of the composition.

* * * * *